United States Patent [19]

Blondelle et al.

[11] Patent Number: 5,624,902
[45] Date of Patent: Apr. 29, 1997

[54] PEPTIDE INHIBITORS OF CALMODULIN

[75] Inventors: Sylvie E. Blondelle, San Diego; Richard A. Houghten, Del Mar; Enrique Perez-Paya, San Diego, all of Calif.

[73] Assignee: Torrey Pines Institute for Molecular Studies, San Diego, Calif.

[21] Appl. No.: 485,396

[22] Filed: Jun. 7, 1995

[51] Int. Cl.$^6$ .............................. A61K 38/08; C07K 7/06
[52] U.S. Cl. .................................. 514/17; 530/329
[58] Field of Search ........................ 530/329; 514/17

[56] References Cited

U.S. PATENT DOCUMENTS

| | | | |
|---|---|---|---|
| 2,645,640 | 7/1953 | Charpentier | 260/242 |
| 4,117,118 | 9/1978 | Harri et al. | 424/177 |
| 4,758,559 | 7/1988 | Wasley et al. | 514/211 |
| 5,182,262 | 1/1993 | Leto | 514/13 |
| 5,340,565 | 8/1994 | Pero | 424/10 |
| 5,480,903 | 1/1996 | Piggott | 514/422 |
| 5,532,337 | 7/1996 | Hayashi et al. | 530/350 |

OTHER PUBLICATIONS

Hait et al., "The effect of calmodulin inhibitors with bleomycin on the treatment of patients with high grade gliomas." *Cancer Res.*, 6636–6640 (1990).

Hidaka et al., "N–(6-Aminohexyl)–5–chloro– 1–naphthalenesulfonamide, a calmodulin antagonist, inhibits cell proliferation." *Proc. Natl. Acad. Sci. USA*, 78(7):4354–4357 (1981).

Polak et al., "A novel calmodulin antagonist, CGS 9343B, modulates calcium–dependent changes in neurite outgrowth and growth cone movements." *J. of Neuroscience*, 11(2):534–542 (1991).

Sharma and Wang, "Preparation and assay of the $Ca^{2+}$ –dependent modulator protein." *Advances in Cyclic Nucleotide Res.*, 10;187–198 (1979).

Schuller et al., "Successful chemotherapy of experimental neuroendocrine lung tumors in hamsters with an antagonist of $Ca^{2+}$/calmodulin." *Cancer Res.*, 50:1645–1649 (1990).

Wallace et al., "Assay of calmodulin by $Ca^{2+}$–dependent phosphodiesterase." *Methods in Enzymology*, 102;39–47 (1983).

*Primary Examiner*—Jeffrey E. Russel
*Assistant Examiner*—Kathleen Carroll
*Attorney, Agent, or Firm*—Campbell & Flores LLP

[57] ABSTRACT

The present invention relates to novel family of peptides which inhibit calmodulin and which have the general structure Ac-(D)Leu-A1-B2-C3-D4-E5-NH$_2$, wherein A1 is (D)Gln or (D)Trp, B2 is (D)Arg or (D)Ile, C3 is (D)Ile or (D)His, D4 is (D)Leu or (D)His and E5 is (D)Trp or (D)Arg. The novel peptides can be used to inhibit the activity of calmodulin. In addition, the present invention relates to pharmaceutical compositions comprising a pharmaceutically acceptable carrier and a calmodulin-inhibitor peptide. These compositions can be used to treat calmodulin related disorders.

8 Claims, 1 Drawing Sheet

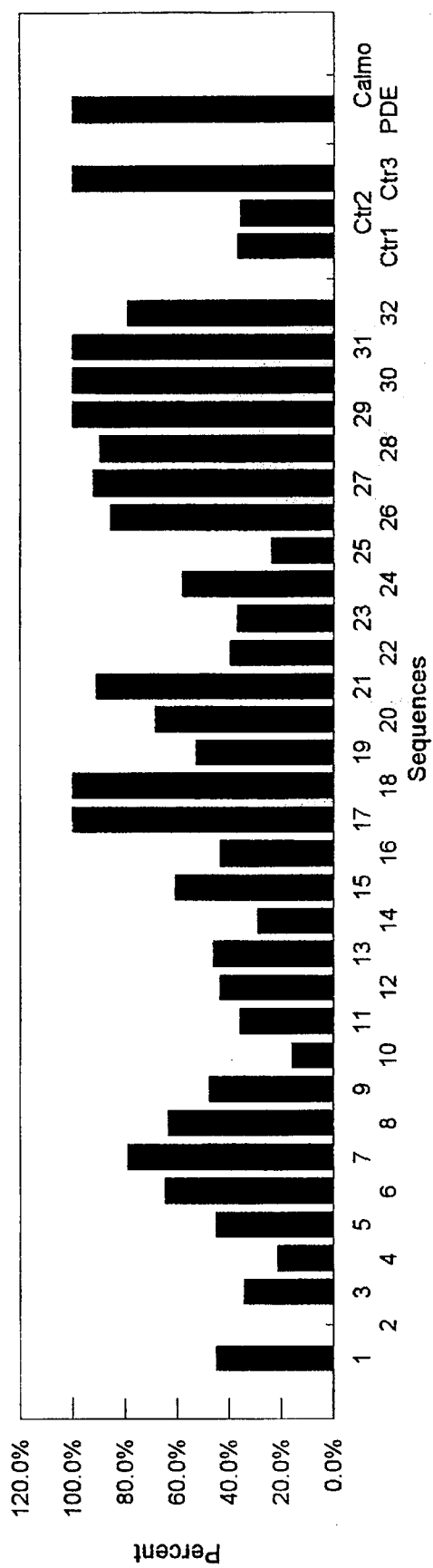

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:

(A) LENGTH: 6 amino acids
(B) TYPE: amino acid
(D) TOPOLOGY: linear (ix) FEATURE:
    (A) NAME/KEY: Peptide
    (B) LOCATION: 1
    (D) OTHER INFORMATION: /note= "Amino acid is acetylated at the N- terminal."

(ix) FEATURE:
    (A) NAME/KEY: Peptide
    (B) LOCATION: 6
    (D) OTHER INFORMATION: /note= "Amino acid is amidated at the C- terminal."

(xi) SEQUENCE DESCRIPTION: SEQ ID NO:1:

Phe  Ile  Ile  Trp  Phe  Glu
1                5

PEPTIDE INHIBITORS OF CALMODULIN

BACKGROUND OF THE INVENTION

1. Field of the Invention

The present invention relates generally to the fields of peptide chemistry and molecular pathology and, more specifically, to novel peptides which bind to calmodulin.

2. Background Information

Calcium is one of the "second messengers" which relays chemical and electrical signals within a cell. This signal transduction and, hence the regulation of biological processes, involves interaction of calcium ions with high-affinity calcium-binding proteins. One such protein is the ubiquitous intracellular receptor protein calmodulin.

Upon calcium binding, calmodulin interacts with a number of protein targets in a calcium dependent manner, thereby altering a number of complex biochemical pathways that can affect the overall behavior of cells. The calcium-calmodulin complex controls the biological activity of more than thirty different proteins including several enzymes, ion transporters, receptors, motor proteins, transcription factors, and cytoskeletal components in eukaryotic cells.

Since calmodulin plays such a fundamental role in cell biology, agents that inhibit or alter its action can have important pharmacological effects. Further, an understanding of the mechanism by which these drugs alter calmodulin-dependent actions can suggest new pharmacological approaches to alter physiological or pathological processes. The discovery of selective pharmacological agents that interfere with the actions of calmodulin can provide a means to explore the physiological role of the calcium-binding protein and can provide new therapeutic agents.

A number of calmodulin targeted compounds are known and used for a variety of therapeutic applications. For instance, chlorpromazine ("THORAZINE"®) and related phenothiazine derivatives, disclosed, for example, in U.S. Pat. No. 2,645,640, are calmodulin antagonists useful as tranquilizers and sedatives. Naphthalenen-sulfonamides, also calmodulin antagonists, are known to inhibit cell proliferation, as disclosed, for example, in Hidaka et al., *PNAS*, 78:4354–4357, (1981) and are useful as antitumor agents. In addition, the cyclic peptide cyclosporin A ("SANDIMMUNE"®), disclosed in U.S. Pat. No. 4,117, 118, is as an immunosuppressive agent which is thought to work by inhibiting calmodulin mediated responses in lymphoid cells.

Many of the known calmodulin inhibitors have additional, undesirable biological effects when administered at concentrations sufficient to block calmodulin. The undesirable effects are usually negative side effects, such as toxicity, or non-specific binding to other proteins or receptors, as described, for example, in Polak et al. *J. Neurosci.*, 11:534–542, (1991). A specific example is the toxic side effects from cyclosporin A. Therefore, a need exists for calmodulin targeted agents, and in particular calmodulin antagonists which inhibit calmodulin without having additional, undesirable biological side effects, and especially ones which do not have toxic side effects. This invention satisfies these needs and provides related advantages as well.

SUMMARY OF THE INVENTION

Disclosed are calmodulin-inhibitory peptides having the general structure Ac-(D)Leu-A1-B2-C3-D4-E5-NH$_2$, wherein A1 is (D)Gln or (D)Trp, B2 is (D)Arg or (D)Ile, C3 is (D)Ile or (D)His, D4 is (D)Leu or (D)His and E5 is (D)Trp or (D)Arg. These novel peptides can be used to inhibit the activity of calmodulin.

In addition, the present invention relates to pharmaceutical compositions comprising a pharmaceutically acceptable carrier and a calmodulin-inhibitory peptide. These pharmaceutical compositions can be used to treat calmodulin-related disorders as provided by the present invention.

BRIEF DESCRIPTION OF THE DRAWINGS

FIG. 1 shows the inhibitory effect of the peptides of the present invention on calmodulin activity at 50 µM peptide concentration in a calcium-dependent phosphodiesterase assay.

DETAILED DESCRIPTION OF THE INVENTION

The present invention generally relates to novel calmodulin inhibitor peptides having the general structure Ac-(D) Leu-A1-B2-C3-D4-E5-NH$_2$, wherein A1 is (D)Gln or (D)Trp, B2 is (D)Arg or (D)Ile, C3 is (D)Ile or (D)His, D4 is (D)Leu or (D)His, and E5 is (D)Trp or (D)Arg.

In one embodiment of the present invention, the peptides specifically have (D)Gln at position A1, and are, therefore, peptides which fall within the scope of the formula Ac-(D) Leu-(D)Gln-B2-C3-D4-E5-NH$_2$, where, again, B2 is (D)Arg or (D)Ile, C3 is (D)Ile or (D)His, D4 is (D)Leu or (D)His, and, E5 is (D)Trp or (D)Arg.

In further embodiments of when A1 is (D)Gln, B2 can be either (D)Arg or (D)Ile, thereby providing peptides within the structures Ac-(D)Leu-(D)Gln-(D)Arg-C3-D4-E5-NH$_2$, and Ac-(D)Leu-(D)Gln-(D)Ile-C3-D4-E5-NH$_2$, wherein for both genera C3 is (D)Ile or (D)His, D4 is (D)Leu or (D)His, and E5 is (D)Trp or (D)Arg.

Also when A1 is (D)Gln, the present invention provides additional embodiments where the peptides have the general structures Ac-(D)Leu-(D)Gln-(D)Arg-(D)Ile-D4-E5-NH$_2$, Ac-(D)Leu-(D)Gln-(D)Arg-(D)His-D4-E5-NH$_2$, Ac-(D) Leu-(D)Gln-(D)Ile-(D)Ile-D4-E5-NH$_2$ and Ac-(D)Leu-(D) Gln-(D)Ile-(D)His-D4-E5-NH$_2$, wherein for each of these formulae D4 is (D)Leu or (D)His and E5 is (D)Trp or (D)Arg.

In additional embodiments when A1 is (D)Gln, the present invention provides peptides described by the formulas Ac-(D)Leu-(D)Gln-(D)Arg-(D)Ile-(D)Leu-E5-NH$_2$, Ac-(D)Leu-(D)Gln-(D)Arg-(D)Ile-(D)His-E5-NH$_2$, Ac-(D) Leu-(D)Gln-(D)Arg-(D)His-(D)Leu-E5-NH$_2$, Ac-(D)Leu-(D)Gln-(D)Arg-(D)His-(D)His-E5-NH$_2$, Ac-(D)Leu-(D) Gln-(D)Ile-(D)Ile-(D)Leu-E5-NH$_2$, Ac-(D)Leu-(D)Gln-(D) Ile-(D)Ile-(D)His-E5-NH$_2$, Ac-(D)Leu-(D)Gln-(D)Ile-(D) His-(D)Leu-E5-NH$_2$, and Ac-(D)Leu-(D)Gln-(D)Ile-(D) His-(D)His-E5-NH$_2$.

In yet other embodiments of the instant invention, the peptides specifically have (D)Trp at position A1. In one embodiment where A1 is (D)Trp, the peptides have the general structure (D)Leu-(D)Trp-B2-C3-D4-E5-NH$_2$, wherein B2 is (D)Arg or (D)Ile, C3 is (D)Ile or (D)His, D4 is (D)Leu or (D)His, and E5 is (D)Trp or (D)Arg.

In further embodiments of when A1 is (D)Trp, B2 can be either (D)Arg or (D)Ile, thereby providing peptides within the structures Ac-(D)Leu-(D)Trp-(D)Arg-C3-D4-E5-NH$_2$ and Ac-(D)Leu-(D)Trp-(D)Ile-C3-D4-E5-NH$_2$, wherein for both genera C3 is (D)Ile or (D)His, D4 is (D)Leu or (D)His, and E5 is (D)Trp or (D)Arg.

Also when A1 is (D)Trp, the present invention provides additional embodiments where the peptides have the general structures Ac-(D)Leu-(D)Trp-(D)Arg-(D)Ile-D4-E5-NH$_2$, Ac-(D)Leu-(D)Trp-(D)Arg-(D)His-D4-E5-NH$_2$, Ac-(D)Leu-(D)Trp-(D)Ile-(D)Ile-D4-E5-NH$_2$, and Ac-(D)Leu-(D)Trp-(D)Ile-(D)His-D4-E5-NH$_2$, wherein for each of these formulae D4 is (D)Leu or (D)His and E5 is (D)Trp or (D)Arg.

In additional embodiments when A1 is (D)Trp, the present invention provides peptides described by the formulas Ac-(D)Leu-(D)Trp-(D)Arg-(D)Ile-(D)Leu-E5-NH$_2$, Ac-(D)Leu-(D)Trp-(D)Arg-(D)Ile-(D)His-E5-NH$_2$, Ac-(D)Leu-(D)Trp-(D)Arg-(D)His-(D)Leu-E5-NH$_2$, Ac-(D)Leu-(D)Trp-(D)Arg-(D)His-(D)His-E5-NH$_2$, Ac-(D)Leu-(D)Trp-(D)Ile-(D)Ile-(D)Leu-E5-NH$_2$, Ac-(D)Leu-(D)Trp-(D)Ile-(D)Ile-(D)His-E5-NH$_2$, Ac-(D)Leu-(D)Trp-(D)Ile-(D)His-(D)Leu-E5-NH$_2$, and Ac-(D)Leu-(D)Trp-(D)Ile-(D)His-(D)His-E5-NH$_2$.

Peptides encompassed by the formulas described above which are provided by the present invention include the following:
Ac-(D)Leu-(D)Gln-(D)Arg-(D)Ile-(D)Leu-(D)Trp-NH$_2$;
Ac-(D)Leu-(D)Gln-(D)Arg-(D)Ile-(D)Leu-(D)Arg-NH$_2$;
Ac-(D)Leu-(D)Gln-(D)Arg-(D)Ile-(D)His-(D)Trp-NH$_2$;
Ac-(D)Leu-(D)Gln-(D)Arg-(D)Ile-(D)His-(D)Arg-NH$_2$;
Ac-(D)Leu-(D)Gln-(D)Arg-(D)His-(D)Leu-(D)Trp-NH$_2$;
Ac-(D)Leu-(D)Gln-(D)Arg-(D)His-(D)Leu-(D)Arg-NH$_2$;
Ac-(D)Leu-(D)Gln-(D)Arg-(D)His-(D)His-(D)Trp-NH$_2$;
Ac-(D)Leu-(D)Gln-(D)Arg-(D)His-(D)His-(D)Arg-NH$_2$;
Ac-(D)Leu-(D)Gln-(D)Ile-(D)Ile-(D)Leu-(D)Trp-NH$_2$;
Ac-(D)Leu-(D)Gln-(D)Ile-(D)Ile-(D)Leu-(D)Arg-NH$_2$;
Ac-(D)Leu-(D)Gln-(D)Ile-(D)Ile-(D)His-(D)Trp-NH$_2$;
Ac-(D)Leu-(D)Gln-(D)Ile-(D)Ile-(D)His-(D)Arg-NH$_2$;
Ac-(D)Leu-(D)Gln-(D)Ile-(D)His-(D)Leu-(D)Trp-NH$_2$;
Ac-(D)Leu-(D)Gln-(D)Ile-(D)His-(D)Leu-(D)Arg-NH$_2$;
Ac-(D)Leu-(D)Gln-(D)Ile-(D)His-(D)His-(D)Trp-NH$_2$;
Ac-(D)Leu-(D)Gln-(D)Ile-(D)His-(D)His-(D)Arg-NH$_2$;
Ac-(D)Leu-(D)Trp-(D)Arg-(D)Ile-(D)Leu-(D)Trp-NH$_2$;
Ac-(D)Leu-(D)Trp-(D)Arg-(D)Ile-(D)Leu-(D)Arg-NH$_2$;
Ac-(D)Leu-(D)Trp-(D)Arg-(D)Ile-(D)His-(D)Trp-NH$_2$;
Ac-(D)Leu-(D)Trp-(D)Arg-(D)Ile-(D)His-(D)Arg-NH$_2$;
Ac-(D)Leu-(D)Trp-(D)Arg-(D)His-(D)Leu-(D)Trp-NH$_2$;
Ac-(D)Leu-(D)Trp-(D)Arg-(D)His-(D)Leu-(D)Arg-NH;
Ac-(D)Leu-(D)Trp-(D)Arg-(D)His-(D)His-(D)Trp-NH$_2$;
Ac-(D)Leu-(D)Trp-(D)Arg-(D)His-(D)His-(D)Arg-NH$_2$;
Ac-(D)Leu-(D)Trp-(D)Ile-(D)Ile-(D)Leu-(D)Trp-NH$_2$;
Ac-(D)Leu-(D)Trp-(D)Ile-(D)Ile-(D)Leu-(D)Arg-NH$_2$;
Ac-(D)Leu-(D)Trp-(D)Ile-(D)Ile-(D)His-(D)Trp-NH$_2$;
Ac-(D)Leu-(D)Trp-(D)Ile-(D)Ile-(D)His-(D)Arg-NH$_2$;
Ac-(D)Leu-(D)Trp-(D)Ile-(D)His-(D)Leu-(D)Trp-NH$_2$;
Ac-(D)Leu-(D)Trp-(D)Ile-(D)His-(D)Leu-(D)-Arg-NH$_2$;
Ac-(D)Leu-(D)Trp-(D)Ile-(D)His-(D)His-(D)Trp-NH$_2$; and
Ac-(D)Leu-(D)Trp-(D)Ile-(D)His-(D)His-(D)Arg-NH$_2$.

In the above formulae and exemplified peptides, the amino acids are indicated by the well known and commonly used three letter code and (D) designates an amino acid having the "D" configuration, as opposed to the naturally occurring L-amino acids. One skilled in the art would know that one or more amino acids within the exemplified peptides could be modified or substituted, as for example, by a conservative amino acid substitution of one or more of the specific amino acids shown in the specifically exemplified peptides. A conservative amino acid substitution change can include, for example, the substitution of one acidic amino acid for another acidic amino acid, of one hydrophobic amino acid for another hydrophobic amino acid or other conservative substitutions known in the art, including the use of non-naturally occurring amino acids, such as (D)norleucine ((D)Nle) for leucine or (D)ornithine (Orn) or (D) homoArginine (homoArg) for (D)Arg.

In addition to the above types of modifications or substitutions, a mimic of one or more amino acids, otherwise known as a peptide mimetic or peptidomimetic, can also be used. As used herein, the term "mimic" means an amino acid or an amino acid analog that has the same or similar functional characteristic of an amino acid. Thus, for example, a (D)arginine analog can be a mimic of (D)arginine if the analog contains a side chain having a positive charge at physiological pH, as is characteristic of the guanidinium side chain reactive group of arginine. A peptide mimetic or peptidomimetic is an organic molecule that retains similar peptide chain pharmacophore groups as are present in the corresponding peptide.

The substitution of amino acids by non-naturally occurring amino acids and peptidomimetics as described above can enhance the overall activity or other properties of an individual peptide based on the modifications to the side chain functionalities. For example, these types of alterations to the exemplified peptides can enhance the peptide's stability to enzymatic breakdown or increase biological activity or decrease immunogenicity.

One skilled in the art, using the above formulae, can easily synthesize the peptides of this invention. Standard procedures for preparing synthetic peptides are well known in the art. The novel peptides can be synthesized using: the solid phase peptide synthesis (SPPS) method of Merrifield (*J. Am. Chem. Soc.*, 85:2149 (1964), which is incorporated herein by reference) or modifications of SPPS; or, the peptides can be synthesized using standard solution methods well known in the art (see, for example, Bodanzsky, M., *Principles of Peptide Synthesis* 2nd revised ed. (Springer-Verlag, 1988 and 1993), which is incorporated herein by reference). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc. Natl. Acad. Sci., U.S.A.* 82:5131 (1985), which is incorporated herein by reference.

The peptides can be synthesized using amino acids or amino acid analogs, the active groups of which are protected as necessary using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenylacetamido methyl and 4-(hydroxymethyl)phenoxymethyl-copoly(styrene-1% divinylbenzene) (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

In the formulae and exemplified peptides, "Ac" indicates an acetyl group at the amino terminus and "NH$_2$" means an amide group is at the carboxy terminus. Peptides can be manipulated, for example, while still attached to a resin to obtain N-terminal modified compounds such as an acetylated peptide or can be removed from the resin using hydrogen fluoride or an equivalent cleaving reagent and then modified. Compounds synthesized containing the C-terminal carboxy group (Wang resin) can be modified after cleavage from the resin or, in some cases, prior to solution phase synthesis. Methods for modifying the N-terminus or C-terminus such as methods for acetylation of the N-terminus or methods for amidation of the C-terminus are well known in the art.

A newly synthesized peptide can be purified using: a method such as reverse phase high performance liquid chromatography (RP-HPLC), chromatofocusing, other methods of separation based on the size or charge of the peptide, or, by immunopurification techniques. Furthermore, the purified peptide can be characterized using these and other well known methods such as amino acid analysis and mass spectrometry.

After manufacture, the peptides of the present invention can be assayed for calmodulin inhibiting and related activity using, for example, a calcium-dependent phosphodiesterase assay, such as that described in the ensuing Example, or those described by Sharma et al., *Adv. Cyclic Nucleotide Res.*, 10:187–189, (1979), or Wallace et al. *Methods Enzymol.*, 102:39–47, (1983), both of which are incorporated herein by reference. In this assay, calmodulin can be assayed by its ability to stimulate phosphodiesterase activity as determined by a two-step assay procedure illustrated by reactions (1) and (2).

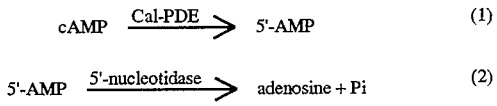

During the first step of the assay cyclic adenosine 3'5'-monophosphate (cAMP) is incubated with calcium-activated phosphodiesterase (Cal-PDE), which hydrolyses the 3' bond producing adenosine 5'-monophosphate (5'-AMP). During the second step 5'-AMP is quantitatively converted into adenosine and inorganic phosphate (Pi) through the action of a 5'-nucleotidase. The reaction is followed by the measurement of the Pi formed by reading the absorbance at 660 NM after reacting with ammonium molybdate. The amount of Pi formed is directly related to the phosphodiesterase activity which depends on the level of activation by calmodulin.

As an alternative or additional assay to that described above, is the myosin light chain kinase assay, as described, for example, by Polak et al. *J. Neurosci.*, 11:534–554, (1991), which are incorporated herein by reference.

The activity of the peptides of present invention involves inhibiting the effects of calmodulin. That is, the peptides of the present invention are calmodulin inhibitors or antagonists. Therefore, also provided by the present invention is a method of inhibiting calmodulin activity by contacting calmodulin with peptides of the present invention. As used herein, the term "inhibiting" has its common meaning, such as to mean reducing, restraining, repressing, or the like, or completely prohibiting or forbidding, calmodulin activity.

As used herein, the term "contact" is used in its broadest sense to mean either direct contact or indirect contact, either of which can involve chemical interaction between calmodulin and a calmodulin-inhibitory peptide of the present invention, for example, ionic interaction between calmodulin protein and a peptide of the present invention.

Recent advances in methods for the preparation and screening of a large numbers of individual peptides has enabled a large number of peptides to be used in all areas of biomedical research. Even with these advances, however, basic research and drug discovery has been limited by the availability of the requisite large number of diverse calmodulin-targeted compounds required to study calmodulin activity. Thus, a need exists for large numbers of individual peptides for use in biomedical research, including those for the study of calmodulin-protein interactions. The present invention provides a relatively large number of calmodulin-inhibitory peptides for use in such biomedical research.

In addition to the peptides' utility in in vitro screening methods, the peptides are also useful in vivo. For example, the peptides of the present invention can be used in vivo diagnostically for the location of calmodulin.

The peptides of the present invention can also be used for treating a subject having a calmodulin-related disorder. As used herein, the term "treating" means reducing or alleviating one or more symptoms or conditions associated with a particular calmodulin-related disorder.

As used herein, the phrase "calmodulin-related disorder" means any abnormality of function or condition associated with the activity or levels or compartmentalization of the calmodulin protein. Such disorders include, but are not limited to, organ damage, autoimmune disorders, psychotic disorders, tumors and drug induced dysfunction, such as negative side effects subsequent to administration of pharmaceuticals. For example, organ or tissue transplantation can result in autoimmune disorders, such as tissue graft (allograft) rejections.

It is well known, as described above, that calmodulin-targeted compounds which are antagonists, can be used as immunosuppressive agents. In addition, also as described above, such compounds are widely used as sedative or anti-psychotic agents. Furthermore, there is evidence that calmodulin antagonists are useful for the treatment of some malignant tumors, particularly those of the central nervous system, as well as lung tumors. The antitumor activity of calmodulin antagonists, as well as successful chemotherapy using the same, has been described, for example, in, Sculler et al. *Cancer Res.*, 50:1645–1649, (1990), Hait et al. *Cancer Res.*, 50:6636–6640, (1990), both of which are incorporated herein by reference. U.S. Pat. No. 5,340,565, which is incorporated herein by reference, additionally describes the use of calmodulin antagonists or inhibitors as agents which enhance the effectiveness of a chemotherapeutic agent or radiation treatment. Described therein is a method of inhibiting or killing a tumor or cancer cell in a human patient undergoing radiation therapy or chemotherapy, for example with such chemotherapeutic agents as cisplatin ("PLATINOL"®), by additionally administering a calmodulin binding agent which inhibits calmodulin activity.

In addition, the peptides of the present invention can be used for treating a subject experiencing negative side effects from the administration of other pharmaceuticals, such as those drugs that disrupt the body's calcium homeostasis. Co-administration of peptides of the present invention would be to counter-effect iatrogenically caused dysfunction of calcium metabolism.

For use in the above-described therapeutic applications, as well as other uses known in the art, the invention also relates to pharmaceutical compositions comprising a calmodulin-inhibitory peptide of the present invention and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters.

A pharmaceutically acceptable carrier can contain physiologically acceptable compounds that act, for example, to stabilize the calmodulin-inhibitory peptide or increase the absorption of the peptide. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration and on the particular physio-chemical characteristics of the specific peptide.

Methods of administering a pharmaceutical are well known in the art. One skilled in the art would know that a pharmaceutical composition comprising a peptide of the present invention can be administered to a subject by various routes including, for example, orally, intravaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment or powder, or active, for example, using a nasal spray or inhalant. A peptide also can be administered as a topical spray, in which case one component of the composition is an appropriate propellant. The pharmaceutical composition also can be incorporated, if desired, into liposomes, microspheres or other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carders that are relatively simple to make and administer. Administration can be effected continuously or intermittently and will vary with the subject and is dependent on the type of treatment and potency of the peptide used.

In order to inhibit the biological activity of a calmodulin, the calmodulin-inhibitory peptide must be administered in an effective dose, which is termed herein as "pharmaceutically effective amount." The effective dose will, of course, depend on the mode of administration. For example, Schuller et al., supra, discloses a range of about 10 to about 35 mg/kg body weight for calmodulin antagonists used in cancer treatment. The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a calmodulin inhibitory peptide required to obtain an effective dose in a subject depends on many factors including the age and general health of the subject as well as the route of administration and the number of treatments to be administered. In view of these factors, the skilled artisan would adjust the particular dose so as to obtain an effective dose for inhibiting calmodulin.

The following example is intended to illustrate but not limit the present invention.

EXAMPLE I

Peptides Which Inhibit Calmodulin

This example describes the peptides which are inhibitors of calmodulin activity.

Individual peptides were identified as capable of inhibiting calmodulin by the above, and in more detail below, described calcium-dependent phosphodiesterase assay. In addition, $IC_{50}$ values were determined for many of the peptides as described below.

The individual peptides were initially identified from a synthetic combinatorial library (SCL). SCLs made up of mixtures of tens of millions of different peptides can be used to rapidly identify individual, active compounds. Since the libraries are in solution (i.e., not attached to a bead, pin, phage, glass, etc.) they can be screened in virtually any assay system. All the calmodulin inhibitor peptides were initially prepared and contained within a positional-scanning synthetic combinatorial library (PS-SCL). Screening of an all D-amino acid acetylated 5× peptide library in a positional scanning format was done with the calcium-dependent phosphodiesterase assay to determine a peptides' percent inhibition on calmodulin activity at a 2 mg/ml concentration. From this screening 32 peptides were identified and each individually synthesized and tested again in the calcium-dependent phosphodiesterase assay at a concentration of 50 µM, as described in more detail below.

Calcium-Dependent Phosphodiesterase Assay

To sample assay tubes were added the following components: assay buffer, 25 µl; $CaCl_2$, 5 µl; 5'-nucleotidase, 7.5 µl (stock solution is 10 units/ml); calmodulin 5 units; calmodulin inhibitor peptides to obtain the desired final concentration of 50 µM. The volume was then made up to 200 µl with water. Control blanks were prepared replacing the peptides with water. The added components were thoroughly mixed and the tubes incubated at 30° C. for 10 min. Then, 25 µl of cAMP at 10.8 mM was added and incubated for 90 min at 30° C. The reaction was stopped by the addition of 50 µl of 55% trichloroacetic acid (TCA). The samples were centrifuged to remove the protein precipitate and the 50 µl of the supernatant was withdrawn for phosphate measurement. To the supernatant aliquot, 50 µl ammonium molybdate (0.55% in 1.1N sulfuric acid) was added, followed by the addition of 5 µl of reducing agent (24 g sodium bisulfite, 2.4 g sodium sulfite, 0.5 g of 1-amino-2-naphthol-4-sulfonic acid in 200 ml of water), and the contents were mixed by vortexing. The absorbance of the solution were read at 660 nm using water as a blank, identified as control "Calmo," as discussed in more detail below.

The two controls used, one without and one with calmodulin in the assay were as follows, as indicated in FIG. 1 and Table 1: (1) PDE: phosphodiesterase (PDE) without calmodulin which represents 100% inhibition, since no activation can occur, and (2) Calmo: PDE being activated by calmodulin without the addition of any peptide (the water blank control mentioned above) which represents 0% inhibition. Three additional peptide controls were used, termed Ctr 1, Ctr 2 and Ctr 3 in FIG. 1, which correspond to the three peptides: Ac-(D)Phe-(D)Phe-(D)His-(D)-Met-(D)Met-(D)Pro-NH$_2$, Ac-(D)Asp-(D)His-(D)Phe-(D)Met-(D)Met-(D)-Ala-NH$_2$, and Ac-Phe-Ile-Ile-Trp-Phe-Glu-NH$_2$ (SEQ ID NO:1), respectively, in Table 1. These three peptides commonly used in every assay as control of reproducibility of the assay.

In addition to the calcium-dependent phosphodiesterase assay data, $IC_{50}$ values were determined for many of the peptides. The assay carried out for the determination in the $IC_{50}$ values differed from the above screening assay by the concentration of the peptides being tested. Each peptide was assayed for $IC_{50}$ at concentrations of 75 µM, 50 µM and 12.5 µM. The $IC_{50}$ represents the concentration in peptide which inhibit 50% of calmodulin activity.

The $IC_{50}$ values of the following four commercially available calmodulin antagonists were used as references in the determination of the $IC_{50}$ values: (1) W7: N-(6-aminohexyl)-5-chloro-1-naphthalene-sulfonamide; (2)

W13: N-(4-aminobutyl)-5-chloro-2-naphtalenesulfonamide; (3) TFP: trifluoperazine; (4) Calmidasolium: (1-[bis-(4-chlorophenyl)methyl]-3[-2-(2,4-dichlorophenyl)-2[(2,4-dichlorophenyl)methoxy]-ethyl]-1H-imidazolium chloride. The $IC_{50}$ values were calculated using sigmoidal curve software (Graphpad, ISI, San Diego) using the % inhibition at different mixture concentrations (see attached protocol for determination of % inhibition).

FIG. 1 and Table 1 show the inhibitory effect of the peptides, providing both the calcium-dependent phosphodiesterase assay data and $IC_{50}$ values.

Although the invention has been described with reference to the examples provided above, it should be understood that various modifications can be made by those skilled in the art without departing from the invention. Accordingly, the invention is set out in the following claims.

TABLE I

| PEPTIDE | % Inhibition | $IC_{50}$ (μM) |
|---|---|---|
| Ac-(D)Leu-(D)Gln-(D)Arg-(D)Ile-(D)Leu-(D)Trp—NH$_2$ | 44.47 | >50 |
| Ac-(D)Leu-(D)Gln-(D)Arg-(D)Ile-(D)Leu-(D)Arg—NH$_2$ | −13.16 | >50 |
| Ac-(D)Leu-(D)Gln-(D)Arg-(D)Ile-(D)His-(D)Trp—NH$_2$ | 34.21 | 40 |
| Ac-(D)Leu-(D)Gln-(D)Arg-(D)Ile-(D)His-(D)Arg—NH$_2$ | 21.05 | >50 |
| Ac-(D)Leu-(D)Gln-(D)Arg-(D)His-(D)Leu-(D)Trp—NH$_2$ | 44.74 | ND |
| Ac-(D)Leu-(D)Gln-(D)Arg-(D)His-(D)Leu-(D)Arg—NH$_2$ | 64.47 | ND |
| Ac-(D)Leu-(D)Gln-(D)Arg-(D)His-(D)His-(D)Trp—NH$_2$ | 78.95 | ND |
| Ac-(D)Leu-(D)Gln-(D)Arg-(D)His-(D)His-(D)Arg—NH$_2$ | 63.16 | ND |
| Ac-(D)Leu-(D)Gln-(D)Ile-(D)Ile-(D)Leu-(D)Trp—NH$_2$ | 47.37 | >50 |
| Ac-(D)Leu-(D)Gln-(D)Ile-(D)Ile-(D)Leu-(D)Arg—NH$_2$ | 15.79 | >50 |
| Ac-(D)Leu-(D)Gln-(D)Ile-(D)Ile-(D)His-(D)Trp—NH$_2$ | 35.53 | ND |
| Ac-(D)Leu-(D)Gln-(D)Ile-(D)Ile-(D)His-(D)Arg—NH$_2$ | 43.42 | ND |
| Ac-(D)Leu-(D)Gln-(D)Ile-(D)His-(D)Leu-(D)Trp—NH$_2$ | 46.05 | ND |
| Ac-(D)Leu-(D)Gln-(D)Ile-(D)His-(D)Leu-(D)Arg—NH$_2$ | 28.95 | ND |
| Ac-(D)Leu-(D)Gln-(D)Ile-(D)His-(D)His-(D)Trp—NH$_2$ | 60.53 | 76 |
| Ac-(D)Leu-(D)Gln-(D)Ile-(D)His-(D)His-(D)Arg—NH$_2$ | 43.42 | ND |
| Ac-(D)Leu-(D)Trp-(D)Arg-(D)Ile-(D)Leu-(D)Trp—NH$_2$ | 101.32 | 15 |
| Ac-(D)Leu-(D)Trp-(D)Arg-(D)Ile-(D)Leu-(D)Arg—NH$_2$ | 106.58 | 15 |
| Ac-(D)Leu-(D)Trp-(D)Arg-(D)Ile-(D)His-(D)Trp—NH$_2$ | 52.63 | ND |
| Ac-(D)Leu-(D)Trp-(D)Arg-(D)Ile-(D)His-(D)Arg—NH$_2$ | 68.42 | 32 |
| Ac-(D)Leu-(D)Trp-(D)Arg-(D)His-(D)Leu-(D)Trp—NH$_2$ | 90.79 | ≦10 |
| Ac-(D)Leu-(D)Trp-(D)Arg-(D)His-(D)Leu-(D)Arg—NH$_2$ | 39.47 | >50 |
| Ac-(D)Leu-(D)Trp-(D)Arg-(D)His-(D)His-(D)Trp—NH$_2$ | 36.84 | ND |
| Ac-(D)Leu-(D)Trp-(D)Arg-(D)His-(D)His-(D)Arg—NH$_2$ | 57.89 | ND |
| Ac-(D)Leu-(D)Trp-(D)Ile-(D)Ile-(D)Leu-(D)Trp—NH$_2$ | 23.68 | >50 |
| Ac-(D)Leu-(D)Trp-(D)Ile-(D)Ile-(D)Leu-(D)Arg—NH$_2$ | 85.53 | 10 |
| Ac-(D)Leu-(D)Trp-(D)Ile-(D)Ile-(D)His-(D)Trp—NH$_2$ | 92.11 | ≦9 |
| Ac-(D)Leu-(D)Trp-(D)Ile-(D)Ile-(D)His-(D)Arg—NH$_2$ | 89.47 | ND |
| Ac-(D)Leu-(D)Trp-(D)Ile-(D)His-(D)Leu-(D)Trp—NH$_2$ | 102.63 | ND |
| Ac-(D)Leu-(D)TrP-(D)Ile-(D)His-(D)Leu-(D)-Arg—NH$_2$ | 102.63 | 12 |
| Ac-(D)Leu-(D)Trp-(D)Ile-(D)His-(D)His-(D)Trp—NH$_2$ | 102.63 | 24 |
| Ac-(D)Leu-(D)Trp-(D)Ile-(D)His-(D)His-(D)Arg—NH$_2$ | 78.95 | 43 |
| phosphodiesterase (PDE) | 100.00 | — |
| Calmodulin (Calmo) | 0.00 | — |
| Ctr 1: Ac-(D)Phe-(D)Phe-(D)His-(D)-Met-(D)Met-(D)Pro—NH$_2$ | 36.84 | — |
| Ctr 2: Ac-(D)Asp-(D)His-(D)Phe-(D)Met-(D)Met-(D)-Ala—NH$_2$ | 35.53 | — |
| Ctr 3: Ac—Phe—Ile—Ile—Trp—Phe—Glu—NH$_2$ (SEQ ID NO: 1) | 106.58 | — |
| W7 | — | 74 |
| W13 | — | <75 |
| TFP | — | 13 |
| Calmidazolium | — | 9 |

ND = Not Yet Determined

We claim:

1. A peptide having the structure:
Ac-(D)Leu-A1-B2-C3-D4-E5-NH$_2$,
wherein A1 is (D)Gln or (D)Trp;
wherein B2 is (D)Arg or (D)Ile;
wherein C3 is (D)Ile or (D)His;
wherein D4 is (D)Leu or (D)His; and
wherein E5 is (D)Trp or (D)Arg.

2. The peptide of claim 1, having a sequence selected from the group consisting of:
Ac-(D)Leu-(D)Gln-(D)Arg-(D)Ile-(D)Leu-(D)Trp-NH$_2$;
Ac-(D)Leu-(D)Gln-(D)Arg-(D)Ile-(D)Leu-(D)Arg-NH$_2$;
Ac-(D)Leu-(D)Gln-(D)Arg-(D)Ile-(D)His-(D)Trp-NH$_2$;
Ac-(D)Leu-(D)Gln-(D)Arg-(D)Ile-(D)His-(D)Arg-NH$_2$;
Ac-(D)Leu-(D)Gln-(D)Arg-(D)His-(D)Leu-(D)Trp-NH$_2$;
Ac-(D)Leu-(D)Gln-(D)Arg-(D)His-(D)Leu-(D)Arg-NH$_2$;
Ac-(D)Leu-(D)Gln-(D)Arg-(D)His-(D)His-(D)Trp-NH$_2$;
Ac-(D)Leu-(D)Gln-(D)Arg-(D)His-(D)His-(D)Arg-NH$_2$;
Ac-(D)Leu-(D)Gln-(D)Ile-(D)Ile-(D)Leu-(D)Trp-NH$_2$;
Ac-(D)Leu-(D)Gln-(D)Ile-(D)Ile-(D)Leu-(D)Arg-NH$_2$;
Ac-(D)Leu-(D)Gln-(D)Ile-(D)Ile-(D)His-(D)Trp-NH$_2$;
Ac-(D)Leu-(D)Gln-(D)Ile-(D)Ile-(D)His-(D)Arg-NH$_2$;
Ac-(D)Leu-(D)Gln-(D)Ile-(D)His-(D)Leu-(D)Trp-NH$_2$;
Ac-(D)Leu-(D)Gln-(D)Ile-(D)His-(D)Leu-(D)Arg-NH$_2$;
Ac-(D)Leu-(D)Gln-(D)Ile-(D)His-(D)His-(D)Trp-NH$_2$;
Ac-(D)Leu-(D)Gln-(D)Ile-(D)His-(D)His-(D)Arg-NH$_2$;
Ac-(D)Leu-(D)Trp-(D)Arg-(D)Ile-(D)Leu-(D)Trp-NH$_2$;
Ac-(D)Leu-(D)Trp-(D)Arg-(D)Ile-(D)Leu-(D)Arg-NH$_2$;
Ac-(D)Leu-(D)Trp-(D)Arg-(D)Ile-(D)His-(D)Trp-NH$_2$;
Ac-(D)Leu-(D)Trp-(D)Arg-(D)Ile-(D)His-(D)Arg-NH$_2$;
Ac-(D)Leu-(D)Trp-(D)Arg-(D)His-(D)Leu-(D)Trp-NH$_2$;
Ac-(D)Leu-(D)Trp-(D)Arg-(D)His-(D)Leu-(D)Arg-NH$_2$;
Ac-(D)Leu-(D)Trp-(D)Arg-(D)His-(D)His-(D)Trp-NH$_2$;
Ac-(D)Leu-(D)Trp-(D)Arg-(D)His-(D)His-(D)Arg-NH$_2$;
Ac-(D)Leu-(D)Trp-(D)Ile-(D)Ile-(D)Leu-(D)Trp-NH$_2$;
Ac-(D)Leu-(D)Trp-(D)Ile-(D)Ile-(D)Leu-(D)Arg-NH$_2$;
Ac-(D)Leu-(D)Trp-(D)Ile-(D)Ile-(D)His-(D)Trp-NH$_2$;
Ac-(D)Leu-(D)Trp-(D)Ile-(D)Ile-(D)His-(D)Arg-NH$_2$;
Ac-(D)Leu-(D)Trp-(D)Ile-(D)His-(D)Leu-(D)Trp-NH$_2$;
Ac-(D)Leu-(D)Trp-(D)Ile-(D)His-(D)Leu-(D)-Arg-NH$_2$;
Ac-(D)Leu-(D)Trp-(D)Ile-(D)His-(D)His-(D)Trp-NH$_2$; and
Ac-(D)Leu-(D)Trp-(D)Ile-(D)His-(D)His-(D)Arg-NH$_2$.

3. A composition of matter, comprising a peptide and a pharmaceutically acceptable carrier, said peptide having the structure:
Ac-(D)Leu-A1-B2-C3-D4-E5-NH$_2$,
wherein A1 is (D)Gln or (D)Trp;
wherein B2 is (D)Arg or (D)Ile;
wherein C3 is (D)Ile or (D)His;
wherein D4 is (D)Leu or (D)His;
wherein E5 is (D)Trp or (D)Arg.

4. The composition of claim 3, wherein the peptide has a sequence selected from the group consisting of:
Ac-(D)Leu-(D)Gln-(D)Arg-(D)Ile-(D)Leu-(D)Trp-NH$_2$;
Ac-(D)Leu-(D)Gln-(D)Arg-(D)Ile-(D)Leu-(D)Arg-NH$_2$;
Ac-(D)Leu-(D)Gln-(D)Arg-(D)Ile-(D)His-(D)Trp-NH$_2$;
Ac-(D)Leu-(D)Gln-(D)Arg-(D)Ile-(D)His-(D)Arg-NH$_2$;
Ac-(D)Leu-(D)Gln-(D)Arg-(D)His-(D)Leu-(D)Trp-NH$_2$;
Ac-(D)Leu-(D)Gln-(D)Arg-(D)His-(D)Leu-(D)Arg-NH$_2$;
Ac-(D)Leu-(D)Gln-(D)Arg-(D)His-(D)His-(D)Trp-NH$_2$;
Ac-(D)Leu-(D)Gln-(D)Arg-(D)His-(D)His-(D)Arg-NH$_2$;
Ac-(D)Leu-(D)Gln-(D)Ile-(D)Ile-(D)Leu-(D)Trp-NH$_2$;
Ac-(D)Leu-(D)Gln-(D)Ile-(D)Ile-(D)Leu-(D)Arg-NH$_2$;
Ac-(D)Leu-(D)Gln-(D)Ile-(D)Ile-(D)His-(D)Trp-NH$_2$;
Ac-(D)Leu-(D)Gln-(D)Ile-(D)Ile-(D)His-(D)Arg-NH$_2$;
Ac-(D)Leu-(D)Gln-(D)Ile-(D)His-(D)Leu-(D)Trp-NH$_2$;
Ac-(D)Leu-(D)Gln-(D)Ile-(D)His-(D)Leu-(D)Arg-NH$_2$;
Ac-(D)Leu-(D)Gln-(D)Ile-(D)His-(D)His-(D)Trp-NH$_2$;
Ac-(D)Leu-(D)Gln-(D)Ile-(D)His-(D)His-(D)Arg-NH$_2$;
Ac-(D)Leu-(D)Trp-(D)Arg-(D)Ile-(D)Leu-(D)Trp-NH$_2$;
Ac-(D)Leu-(D)Trp-(D)Arg-(D)Ile-(D)Leu-(D)Arg-NH$_2$;
Ac-(D)Leu-(D)Trp-(D)Arg-(D)Ile-(D)His-(D)Trp-NH$_2$;
Ac-(D)Leu-(D)Trp-(D)Arg-(D)Ile-(D)His-(D)Arg-NH$_2$;
Ac-(D)Leu-(D)Trp-(D)Arg-(D)His-(D)Leu-(D)Trp-NH$_2$;
Ac-(D)Leu-(D)Trp-(D)Arg-(D)His-(D)Leu-(D)Arg-NH$_2$;
Ac-(D)Leu-(D)Trp-(D)Arg-(D)His-(D)His-(D)Trp-NH$_2$;
Ac-(D)Leu-(D)Trp-(D)Arg-(D)His-(D)His-(D)Arg-NH$_2$;
Ac-(D)Leu-(D)Trp-(D)Ile-(D)Ile-(D)Leu-(D)Trp-NH$_2$;
Ac-(D)Leu-(D)Trp-(D)Ile-(D)Ile-(D)Leu-(D)Arg-NH$_2$;
Ac-(D)Leu-(D)Trp-(D)Ile-(D)Ile-(D)His-(D)Trp-NH$_2$;
Ac-(D)Leu-(D)Trp-(D)Ile-(D)Ile-(D)His-(D)Arg-NH$_2$;
Ac-(D)Leu-(D)Trp-(D)Ile-(D)His-(D)Leu-(D)Trp-NH$_2$;
Ac-(D)Leu-(D)Trp-(D)Ile-(D)His-(D)Leu-(D)-Arg-NH$_2$;
Ac-(D)Leu-(D)Trp-(D)Ile-(D)His-(D)His-(D)Trp-NH$_2$; and
Ac-(D)Leu-(D)Trp-(D)Ile-(D)His-(D)His-(D)Arg-NH$_2$.

5. A method for treating a calmodulin related disorder, comprising administering to a subject a pharmaceutically effective amount of the composition of claim 3.

6. A method of treating a calmodulin related disorder, comprising administering to a subject a pharmaceutically effective amount of the composition of claim 4.

7. A method of inhibiting calmodulin activity, comprising contacting calmodulin with a peptide having the structure:

Ac-(D)Leu-A1-B2-C3-D4-E5-NH$_2$, wherein A1 is (D)Gln or (D)Trp;

wherein B2 is (D)Arg or (D)Ile;

wherein C3 is (D)Ile or (D)His;

wherein D4 is (D)Leu or (D)His; and wherein E5 is (D)Trp or (D)Arg.

8. The method of inhibiting of claim 7, wherein the peptide has a sequence selected from the group consisting of:

Ac-(D)Leu-(D)Gln-(D)Arg-(D)Ile-(D)Leu-(D)Trp-NH$_2$;
Ac-(D)Leu-(D)Gln-(D)Arg-(D)Ile-(D)Leu-(D)Arg-NH$_2$;
Ac-(D)Leu-(D)Gln-(D)Arg-(D)Ile-(D)His-(D)Trp-NH$_2$;
Ac-(D)Leu-(D)Gln-(D)Arg-(D)Ile-(D)His-(D)Arg-NH$_2$;
Ac-(D)Leu-(D)Gln-(D)Arg-(D)His-(D)Leu-(D)Trp-NH$_2$;
Ac-(D)Leu-(D)Gln-(D)Arg-(D)His-(D)Leu-(D)Arg-NH$_2$;
Ac-(D)Leu-(D)Gln-(D)Arg-(D)His-(D)His-(D)Trp-NH$_2$;
Ac-(D)Leu-(D)Gln-(D)Arg-(D)His-(D)His-(D)Arg-NH$_2$;
Ac-(D)Leu-(D)Gln-(D)Ile-(D)Ile-(D)Leu-(D)Trp-NH$_2$;
Ac-(D)Leu-(D)Gln-(D)Ile-(D)Ile-(D)Leu-(D)Arg-NH$_2$;
Ac-(D)Leu-(D)Gln-(D)Ile-(D)Ile-(D)His-(D)Trp-NH$_2$;
Ac-(D)Leu-(D)Gln-(D)Ile-(D)Ile-(D)His-(D)Arg-NH$_2$;
Ac-(D)Leu-(D)Gln-(D)Ile-(D)His-(D)Leu-(D)Trp-NH$_2$;
Ac-(D)Leu-(D)Gln-(D)Ile-(D)His-(D)Leu-(D)Arg-NH$_2$;
Ac-(D)Leu-(D)Gln-(D)Ile-(D)His-(D)His-(D)Trp-NH$_2$;
Ac-(D)Leu-(D)Gln-(D)Ile-(D)His-(D)His-(D)Arg-NH$_2$;
Ac-(D)Leu-(D)Trp-(D)Arg-(D)Ile-(D)Leu-(D)Trp-NH$_2$;
Ac-(D)Leu-(D)Trp-(D)Arg-(D)Ile-(D)Leu-(D)Arg-NH$_2$;
Ac-(D)Leu-(D)Trp-(D)Arg-(D)Ile-(D)His-(D)Trp-NH$_2$;
Ac-(D)Leu-(D)Trp-(D)Arg-(D)Ile-(D)His-(D)Arg-NH$_2$;
Ac-(D)Leu-(D)Trp-(D)Arg-(D)His-(D)Leu-(D)Trp-NH$_2$;
Ac-(D)Leu-(D)Trp-(D)Arg-(D)His-(D)Leu-(D)Arg-NH$_2$;
Ac-(D)Leu-(D)Trp-(D)Arg-(D)His-(D)His-(D)Trp-NH$_2$;
Ac-(D)Leu-(D)Trp-(D)Arg-(D)His-(D)His-(D)Arg-NH$_2$;
Ac-(D)Leu-(D)Trp-(D)Ile-(D)Ile-(D)Leu-(D)Trp-NH$_2$;
Ac-(D)Leu-(D)Trp-(D)Ile-(D)Ile-(D)Leu-(D)Arg-NH$_2$;
Ac-(D)Leu-(D)Trp-(D)Ile-(D)Ile-(D)His-(D)Trp-NH$_2$;
Ac-(D)Leu-(D)Trp-(D)Ile-(D)Ile-(D)His-(D)Arg-NH$_2$;
Ac-(D)Leu-(D)Trp-(D)Ile-(D)His-(D)Leu-(D)Trp-NH$_2$;
Ac-(D)Leu-(D)Trp-(D)Ile-(D)His-(D)Leu-(D)-Arg-NH$_2$;
Ac-(D)Leu-(D)Trp-(D)Ile-(D)His-(D)His-(D)Trp-NH$_2$; and
Ac-(D)Leu-(D)Trp-(D)Ile-(D)His-(D)His-(D)Arg-NH$_2$.

* * * * *

UNITED STATES PATENT AND TRADEMARK OFFICE
CERTIFICATE OF CORRECTION

PATENT NO. : 5,624,902
DATED : Apr. 29, 1997
INVENTOR(S) : Blondelle et al.

It is certified that error appears in the above-identified patent and that said Letters Patent is hereby corrected as shown below:

In column 7, line 31, please delete "carders" and replace therefor with --carriers--.

In Table I, at the 10$^{th}$ peptide from the bottom of the table, please delete "Ac-(D)Leu-(D)Trp-(D)Ile-(D)Ile-(D)His-(D)Arg-NH$_2$" and replace therefor with --Ac-(D)Leu-(D)Trp-(D)Ile-(D)His-(D)His-(D)Arg-NH$_2$--.

Signed and Sealed this

Sixth Day of February, 2001

Attest:

Q. TODD DICKINSON

Attesting Officer

Director of Patents and Trademarks